United States Patent [19]

Conrow et al.

[11] 4,008,320

[45] Feb. 15, 1977

[54] AMIDOPHENYL-AZO-NAPHTHALENESULFONIC COMPLEMENT INHIBITORS AND METHOD OF USE THEREOF

[75] Inventors: Ransom Brown Conrow, Pearl River; Seymour Bernstein, New City, both of N.Y.; Robert Herman Lenhard, Paramus, N.J.

[73] Assignee: American Cyanamid Company, Stamford, Conn.

[22] Filed: Dec. 12, 1975

[21] Appl. No.: 640,369

[52] U.S. Cl. .................................. 424/226; 260/199
[51] Int. Cl.² .............. C07C 107/06; C07C 107/07
[58] Field of Search ................. 260/199; 424/226

[56] References Cited

UNITED STATES PATENTS

| 3,502,644 | 3/1970 | Nickel et al. | 260/154 |
| 3,558,592 | 1/1971 | Montmollin | 260/199 |

FOREIGN PATENTS OR APPLICATIONS

| 2,150,823 | 6/1972 | Germany | 260/199 |

*Primary Examiner*—Allen B. Curtis
*Attorney, Agent, or Firm*—Jack W. Richards

[57] ABSTRACT

Substituted amidophenyl-azo-naphthalenesulfonic acids and salts useful as complement inhibitors.

17 Claims, No Drawings

AMIDOPHENYL-AZO-NAPHTHALENESULFONIC COMPLEMENT INHIBITORS AND METHOD OF USE THEREOF

CROSS-REFERENCE TO RELATED APPLICATION

This application is related to concurrently filed and copending Application Ser. No. 640,101, filed Dec. 12, 1975.

BACKGROUND OF THE INVENTION

The present invention resides in the concept of certain substituted amidophenyl-azo-naphthalenesulfonic acids and salts and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935–938 (1968); *Scientific American*, 229, (No. 5), 54–66 (1973); *Medical World News*, Oct. 11, 1974, pp. 53–58; 64–66; *Harvey Lectures*, 66, 75–104 (1972); *The New England Journal of Medicine*, 287, 489–495; 545–549; 592–596; 642–646 (1972); *The Johns Hopkins Med. J.* 128, 57–74 (1971); and *Federation Proceedings*, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969).

A variety of substances have been disclosed as inhibiting the complement system, i.e., as complement inhibitors. For example, the compounds 3,3'-ureylenebis [6-(2-amino-8-hydroxy-6-sulfo-1-naphthylazo)] benzenesulfonic acid tetrasodium salt (chlorazol fast pink), heparin and a sulphated dextran have been reported to have an anticomplementary effect, *British Journal of Experimental Pathology*, 33, 327–339 (1952). The compound 8,8'-[ureylenebis [m-phenylenecarbonylimino(4-methyl-m-phenylene)carbonylimino]]di-1,3,5-naphthalenetrisulfonic acid, hexasodium salt (Suramin Sodium) is described as a competitive inhibitor of the complement system, *Clin. Exp. Immunol.*, 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, *Journal of Medicinal Chemistry*, 12, 415–419, 902–905, 1049–1052, 1053–1056 (1969); *Canadian Journal of Biochemistry*, 47, 547–552, (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilson-aminocapronic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunopath*, II, 163–168 (1974); and *J. Allergy Clin. Immunol.*, 53, No. 298–302 (1974).

SUMMARY OF THE INVENTION

It has now been discovered that certain substituted amidophenyl-azo-naphthalenesulfonic compounds interact with the complement reaction sequence, thereby inhibiting complement activity in body fluids.

One aspect of this invention is concerned with compounds having complement inhibiting activity of the general formula (I):

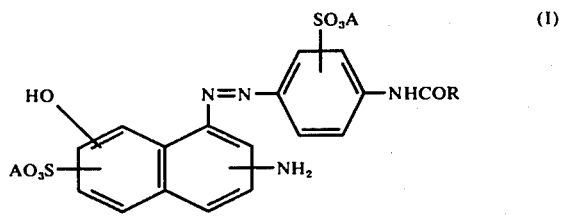

wherein R is selected from the group consisting of $(C_1-C_6)$ alkyl, phenyl, sulfophenyl sodium salt, p-nitrophenyl, and m-fluorophenyl; and A is hydrogen, sodium and potassium, with the proviso that A is identical in the same compound and when A is sodium, the —$SO_3Na$ groups cannot be on the number 2-position of the naphthyl ring system and the number 2-position of the phenyl ring system when the —$NH_2$ group is on the number 6-position of the naphthyl ring system, the —OH group is on the number 4-position of the naphthyl ring system and R is methyl, pentyl or phenyl.

Of particular interest in the above general formula (I) are the group of compounds wherein A is Na (sodium) and within this group, those compounds of most interest are those of general formula (II):

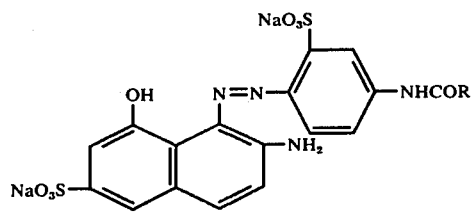

wherein R is selected from the group $(C_2-C_4)$ alkyl, sulfophenyl sodium salt, p-nitrophenyl, and m-fluorophenyl.

Representative compounds encompassed within this invention include, for example, 6-amino-4-hydroxy-5-(2-sulfo-4-p-sulfobenzamidophenylazo)-2-naphthalenesulfonic acid, trisodium salt; 6-amino-4-hydroxy-5-(4-propionamido-2-sulfophenylazo)-2-naphthalenesulfonic acid, disodium salt; 6-amino-4-hydroxy-5-[4-(p-nitrobenzamido)-2-sulfophenylazo]-2-naphthalenesulfonic acid, disodium salt; and 6-amino-5-[4-(m-fluorobenzamido)-2-sulfophenylazo]-4-hydroxy-2-naphthalenesulfonic acid disodium salt.

The closest known compound to those of the present invention, and disclosed as having anticomplementary effect, is the compound 3,3'-ureylenebis[6-(2-amino-8-hydroxy-6-sulfo-1-naphthylazo)]benzenesulfonic acid tetrasodium salt (chlorazol fast pink), *British Journal of Experimental Pathology*, 33, 327–339 (1952). Other known compounds, not disclosed as having anti-complement activity, are the compounds 3-sulfo-7-amino-8-(2'-sulfo-4'-aminophenylazo)-1-naphthol, 5-(4-acetamido-2-sulfophenylazo)-5-amino-4-hydroxy-2-naphthalenesulfonic acid, disodium salt, 6-amino-5-(4-benzamido-2-sulfophenylazo)-4-hydroxy-2-naphthalenesulfonic acid, disodium salt, and 5-(4-pentylamido-2-sulfophenylazo)-5-amino-4-acetamido-2-naphthalenesulfonic acid, disodium salt, all disclosed in *Chemical Abstracts*, 48: 10646h (1954).

Another aspect of this invention is concerned with a method of preparing compounds of formulae (I) and (II) hereinabove which comprises reacting a compound of formula (III):

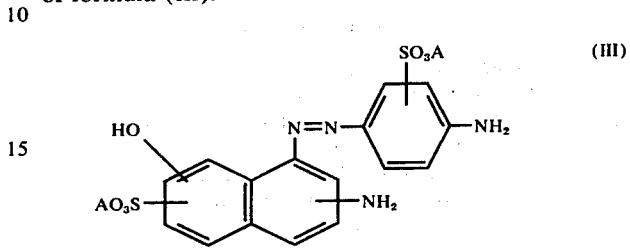

in an aqueous media with an appropriate acid anhydride of the formula:

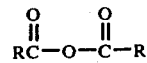

or, in the alternative, treatment of a basic solution of a compound within formula III with an appropriate acid chloride of the formula:

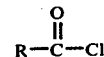

wherein A and R are as defined with reference to formulae (I) and (II) hereinabove. The appropriate aqueous acid anhydride and diamine mixture is stirred at room temperature for a specified time, then is heated to a temperature of between 15°–100° C. and is salted out with sodium acetate trihydrate. After standing at room temperature the product is then filtered and washed copiously with absolute ethanol and ether. The mixture of the diamine with the specific acid chloride in N sodium hydroxide may be acidified with glacial acetic acid and extracted with ether. The aqueous phase is salted with sodium acetate trihydrate. The product is filtered and washed with absolute ethanol and ether. Acidification provides the free acid.

For example, compounds within the present invention and represented by formula (II) may be prepared from the known compound 6-amino-5-(4-amino-2-sulfophenylazo)-4-hydroxy-2-naphthalenesulfonic acid, disodium salt having formula (IV)

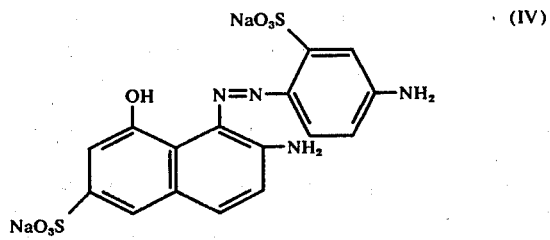

by reacting said compound with an appropriate acid anhydride

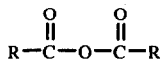

(wherein R is as hereinbefore defined) in an aqueous medium at room temperature for from several minutes to several days. The mixture is heated to 50°–80° C. and the resulting product salted out with sodium acetate trihydrate. Conventional solvent extractions produce the desired product in pure form. Alternatively, compounds within the present invention may also be prepared by reacting 6-amino-5-(4-amino-2-sulfophenylazo)-4-hydroxy-2-naphthalenesulfonic acid, disodium salt with an appropriate acid chloride of the formula

(wherein R is as hereinbefore defined) in a basic medium. Acidification of the reaction mixture, extraction with ether and salting of the aqueous phase with sodium acetate trihydrate produces the desired products.

This invention is also concerned with a method of inhibiting the complement system in a body fluid, such as blood serum, which comprises subjecting body fluid complement to the action of an effective complement inhibiting amount of a compound encompassed within formula (V):

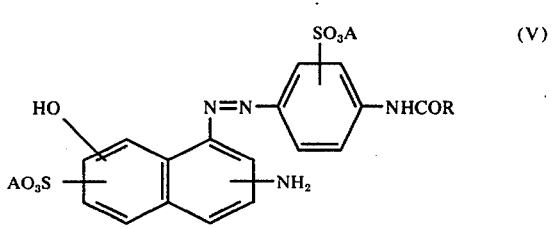

wherein R is selected from the group ($C_1$–$C_6$) alkyl, phenyl, sulfophenyl sodium salt, p-nitrophenyl, and m-fluorophenyl; and A is hydrogen, sodium, potassium, with the proviso that A is identical in the same compound.

Of particular interest in formula (V) are the group of compounds wherein A is sodium and within this group, those compounds of most interest are those of general formula (VI):

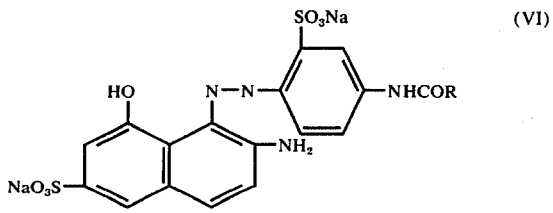

The method of use aspect of this invention is also concerned with a method of inhibiting the complement system in a warm-blooded animal which comprises internally administering to said animal an effective complement inhibiting amount of a compound encompassed within formulae (V) and (VI) hereinabove. Body fluid can include blood, plasma, serum, synovial fluid, cerebrospinal fluid, or pathological accumulations of fluid as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin Sodium, etc.) and inflammatory states induced by the action of bacterial of lysosomal enzymes on the appropriate complement components as for example, inflammation following coronary occlusion. They may also be useful in the treatment of transplant rejection.

DETAILED DESCRIPTION OF THE INVENTION

The following examples will serve to illustrate the invention in more detail.

EXAMPLE 1

Preparation of 6-Amino-5-(4-amino-2-sulfophenylazo)-4-hydroxy-2-naphthalenesulfonic acid, disodium salt A slightly warm solution of 48.0 g of 2-amino-5-nitrobenzenesulfonic acid, sodium salt and 13.8 g of sodium nitrite is prepared in 300 ml of water. This solution is poured over s stirred mixture of 25 ml of concentrated hydrochloric acid, 100 ml of glacial acetic acid and 300 g of ice in a two liter beaker. The resulting solution is kept cold in a stirred ice bath during preparation of a solution of the sodium salt of 7-amino-1-naphthol-3-sulfonic acid (gamma acid). To a solution of 56.2 g of 85% pure 7-amino-1-naphthol-3-sulfonic acid in 100 ml of water and 42.5 ml of 5N sodium hydroxide, is added 61.0 g of sodium acetate trihydrate in 55 ml of water. The resulting solution is poured into the stirred ice cooled diazonium salt solution and stirring is continued at room temperature for 20 minutes. The mixture is then warmed to about 85° C and filtered through diatomaceous earth. The filter is washed with a small amount of water. To the filtrate at about 45° C is added 100 g of sodium hydroxide portionwise, with cooling in an ice bath, to maintain about 50°–60° C. A 150 g amount of sodium acetate trihydrate is then added portionwise with stirring. Stirring is continued overnight then the solution is filtered and washed with 2–100 ml protions of a 33.3% aqueous solution of sodium acetate trihydrate followed by 6–250 ml portions of absolute ethanol. The filtration is continued overnight and the moist cake is slurried twice with ether to remove residual alcohol. The product is then dried in an oven at 105° C to give 6-amino-4-hydroxy-5-(4-nitro-2-sulfophenylazo)-2-naphthalenesulfonic acid, disodium salt.

To a stirred solution of 73.1 g of the above product in 410 ml of water maintained at about 70° C is added 65 g of sodium sulfide nonahydrate portionwise over a 10 minute period and the temperature is raised to 75°–80° C and maintained there for 20 minutes. After the last addition of sodium sulfide, 30 ml of glacial acetic acid is added and the mixture is filtered through diatomaceous earth, then washed with about 150 ml of hot water. The hot filtrate is salted with 300 g of sodium acetate trihydrate with warming, seeding and scratching. The solution is filtered after standing overnight at room temperature, then is washed with 75 ml of a 33.3% aqueous solution of sodium acetate trihydrate. The product is slurried in the funnel with 4–125 ml portions of absolute ethanol and finally is slurried with 2–200 ml portions of ether then is air dried to give 6-amino-5-(4-amino-2-sulfophenylazo)-4-hydroxy-2-naphthalenesulfonic acid, disodium salt.

EXAMPLE 2

6-Amino-4-hydroxy-5-(4-propionamido-2-sulfophenylazo)-2-naphthalenesulfonic acid, disodium salt To a solution of 2.0 g of 6-amino-5-(4-amino-2-sulfophenylazo)-4-hydroxy-2-naphthalenesulfonic acid, disodium salt in 20 ml of water, which is stirring at room temperature, is added 2.0 ml of propionic anhydride and stirring is continued for one hour. The reaction mixture is heated to 80° C and is salted with 10 g of sodium acetate trihydrate. After heating at 90° C the mixture is cooled to room temperature, the product is filtered and washed copiously with absolute ethanol then with ether to obtain a dark powder identified as 6-amino-4-hydroxy-5-(4-sulfophenylazo)-2-naphthalenesulfonic acid, disodium salt.

EXAMPLE 3

6-Amino-4-hydroxy-5-[4-(p-nitrobenzamido)-2-sulfophenylazo]-2-naphthalenesulfonic acid, disodium salt A solution of 2.0 g of 6-amino-5-(4-amino-2-sulfophenylazo)-4-hydroxy-2-naphthalenesulfonic acid, disodium salt in 14.0 ml of N sodium hydroxide is treated with 2.0 g of p-nitrobenzoyl chloride and a few drops of ether. The reaction mixture is shaken for 3 to 4 minutes and then another 7 ml portion of base is added to the reaction mixture. After shaking for 15 minutes the procedure is repeated with an additional 7 ml portion of base. Finally the reaction mixture is acidified with 2 ml of glacial acetic acid, and extracted several times with ether. After the ethereal layer is separated the aqueous phase is salted with 20 g of sodium acetate trihydrate at 55° C with stirring. The reaction mixture is filtered after standing overnight at room temperature and washed with absolute ethanol and ether to give 6-amino-4-hydroxy-5-[4-(p-nitrobenzamido)-2-sulfophenylazo]-2-naphthalenesulfonic acid, disodium salt.

EXAMPLE 4

6-Amino-5-[4-(m-fluorobenzamido)-2-sulfophenylazo]-4-hydroxy-2-naphthalenesulfonic acid, disodium salt To a solution of 2.0 g of 6-amino-5-(4-amino-2-sulfophenylazo)-4-hydroxy-2-naphthelenesulfonic acid, disodium salt in 7 ml of N sodium hydroxide is added 2.0 ml of m-fluorobenzyl chloride and a few drops of ether. The reaction mixture is shaken for 3 to 4 minutes, and another 7 ml portion of base is added to it. After shaking for 15 minutes the procedure is repeated with two additional 7 ml portions of base. Finally, the reaction mixture is acidified with 2 ml of glacial acetic acid, and is extracted several times with ether to remove m-fluorobenzoic acid. After the ethereal layer is separated, the aqueous phase is salted with 15 g of sodium acetate trihydrate and is allowed to stand overnight. The reaction mixture is then centrifuged and decanted several times with absolute ethanol, and several times with ether. Filtration gives 6-amino-5-[4-(m-fluorobenzamido)-2-sulfophenylazo]-4-hydroxy-2-naphthalenesulfonic acid, disodium salt.

EXAMPLE 5

| Preparation of Compressed Tablet | |
|---|---|
| | mg./tablet |
| 5-(4-Acetamido-2-sulfophenylazo)-5-amino-4-hydroxy-2-naphthalenesulfonic acid, disodium salt | 0.5 – 500 |
| Dibasic Calcium Phosphate NF | qs |
| Starch USP | 40 |
| Modified Starch | 10 |
| Magnesium Stearate USP | 1 – 5 |

EXAMPLE 6

| Preparation of Compressed Tablet-Sustained Action | |
|---|---|
| | mg./tablet |
| 6-Amino-4-hydroxy-5-(2-sulfo-4-p-sulfobenzamidophenylazo)-2-naphthalenesulfonic acid, trisodium salt as aluminum lake, micronized | 0.5 – 500 as acid equivalent |
| Dibasic Calcium Phosphate NF | qs |
| Alginic Acid | 20 |
| Starch USP | 35 |
| Magnesium Stearate USP | 1 – 10 |

Complement inhibitor plus aluminum sulfate yields aluminum complement inhibitor. Complement inhibitor content in aluminum lake ranges from 5 – 30%.

EXAMPLE 7

| Preparation of Hard Shell Capsule | |
|---|---|
| | mg./capsule |
| 6-Amino-4-hydroxy-5-(4-propionamido-2-sulfophenylazo)-2-naphthalenesolfonic acid, disodium salt | 0.5 – 500 |
| Lactose, Spray Dried | qs |
| Magnesium Stearate | 1 – 10 |

EXAMPLE 8

| Preparation of Oral Liquid (Syrup) | |
|---|---|
| | % w/v |
| 6-Amino-4-hydroxy-5-[4-p-nitrobenzamido)-2-sulfophenylazo]-2-naphthalenesulfonic acid, disodium salt | 0.05 – 5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 9

| Preparation of Oral Liquid (Elixir) | |
|---|---|
| | % w/v |
| 6-Amino-5-(m-fluorobenzamido)-2-sulfophenylazo]-4-hydroxy-2-naphthalenesulfonic acid, disodium salt | 0.05 – 5 |
| Alcohol USP | 12.5 |
| Glycerin USP | 45.0 |

-continued

Preparation of Oral Liquid (Elixir)

| | % w/v |
|---|---|
| Syrup USP | 20.0 |
| Flavoring Agent | qs |
| Purified Water qs ad | 100.0 |

EXAMPLE 10

Preparation of Oral Suspension (Syrup)

| | % w/v |
|---|---|
| 6-Amino-5-(4-benzamido-2-sulfo-phenylazo)-4-hydroxy-2-naphthalenesulfonic acid, disodium salt as aluminum lake, micronized | 0.05 – 5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 11

Preparation of Injectable Solution

| | % w/v |
|---|---|
| 5-(4-Acetamido-2-sulfophenylazo)-5-amino-4-hydroxy-2-naphthalenesulfonic acid, disodium salt | 0.05 – 5 |
| Benzyl Alcohol N.F. | 0.09 |
| Water for Injection | 100.0 |

EXAMPLE 12

Preparation of Injectable Oil

| | % w/v |
|---|---|
| 5-(4-Acetamido-2-sulfophenylazo)-5-amino-4-hydroxy-2-naphthalenesulfonic acid, disodium salt | 0.05 – 5 |
| Benzyl Alcohol | 1.5 |
| Sesame Oil qs ad | 100.0 |

EXAMPLE 13

Preparation of Injectable Depo Suspension

| | % w/v |
|---|---|
| 6-Amino-4-hydroxy-5-(4-propionamido-2-sulfophenylazo)-2-naphthalenesulfonic acid, disodium salt as aluminum lake, micronized | 0.05 – 5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6 – 8 | qs |
| Water for Injection qs ad | 100.00 |

The compounds of this invention may be administered internally, e.g., orally or parenterally such as intra-articularly, to a warm-blooded animal to inhibit complement in the body fluid of the animal, such inhibition being useful in the amelioration or prevention of those reactions dependent upon the function of complement, such as inglammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every six hours for more rapidly excreted salt, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of sulfonic compound administered can vary over a wide range to provide from about 5 mg./kg. to about 100 mg./kg. of body weight of animal per day. The usual daily dosage for a 70 kg. subject may vary from about 350 mg. to about 3.5 g. Unit doses of the compound can contain from about 0.5 mg. to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety for forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action of predetermined successive action of the enclosed medication. For example, the tablet or pill can comprise an inner dosage, an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powders, packets, granules, wafers, cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor)-In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg./kg. is then reported, unless otherwise stated; (v) Forssman Shock Test — Lethal shock is produced in guinea pigs by an i.v. injection of anit-Forssman antiserum and the harmonic mean death time of treated guinea pigs is compared with that of simultaneous controls; (vi) Complement Level Reduction Test — In this test, the above doses guinea pigs, or others, are bled for serum and the capillary level is determined in undiluted serum by the capillary tube method of U.S. Pat. No. 3,876,376 and compared to undosed control guinea pigs; and (vii) Cap 50 Test — Here, appropriate amount of the test compound are added to a pool of guinea pig serum in vitro, after which the undiluted serum capillary tube assay referred to above is run. The concentration of compound inhibiting 50% is reported.

Table I shows that the substituted amido compounds of the invention possess complement-inhibiting activity.

TABLE I

| Compound | Biological Activity Assay Results | | | |
|---|---|---|---|---|
| | In Vitro | | In Vivo | |
| | 026* | 035 | Forssman | % Reduction Complement |
| 6-Amino-4-hydroxy-5-(4-propionamido-2-sulfophenylazo)-2-naphthalenesulfonic acid, disodium salt | +1** | Neg. | | |
| 6-Amino-5-[4-m-fluorobenzamido-2-sulfophenylazo]-4-hydroxy-2-naphthalenesulfonic acid, disodium salt | Neg. | +1 | | |
| 6-Amino-5-(4-benzamido-2-sulfophenylazo)-4-hydroxy-2-naphthalenesulfonic acid, disodium salt | +2 | Neg. | | |
| 6-Amino-4-hydroxy-5-[4-(p-nitrobenzamido)-2-sulfophenylazo]-2-naphthalenesulfonic acid, disodium salt | +3 | +1 | | |

*Tests identified by code herein.
**Activity 1 well, a serial dilution assay; higher well number indicates higher activity. The serial dilutions are two-fold.

We claim:
1. A compound, 6-amino-4-hydroxy-5-(2-sulfo-4-p-sulfobenzamidophenylazo)-2-naphthalenesulfonic acid, trisodium salt.
2. A compound, 6-amino-4-hydroxy-5-(4-propionamido-2-sulfophenylazo)-2-naphthalenesulfonic acid, disodium salt.
3. A compound, 6-amino-4-hydroxy-5-[4-(p-nitrobenzamido)-2-sulfophenylazo]-2-naphthalenesulfonic acid, disodium salt.
4. A method of inhibiting the complement system in a body fluid which comprises subjecting said body fluid to the action of an effective complement inhibiting amount of a compound of the formula:

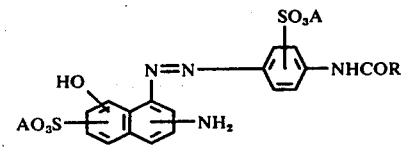

wherein R is selected from the group $(C_1-C_6)$ alkyl, phenyl, sulfophenyl sodium salt, p-nitrophenyl and m-fluorophenyl; and A is hydrogen, sodium and potassium, with the proviso that A is identical in the same compound.
5. A method according to claim 4 wherein the compound is 5-(4-acetamido-2-sulfophenylazo)-5-amino-4-hydroxy-2-naphthalenesulfonic acid, disodium salt.
6. A method according to claim 4 wherein the compound is 6-amino-4-hydroxy-5-(2-sulfo-4-p-sulfobenzamidophenylazo)-2-naphthalenesulfonic acid, trisodium salt.
7. A method according to claim 4, wherein the compound is 6-amino-4-hydroxy-5-(4-propionamido-2-sulfophenylazo)-2-naphthalenesulfonic acid, disodium salt.

8. A method according to claim 4 wherein the compound is 6-amino-4-hydroxy-5-[4-(p-nitrobenzamido)-2-sulfophenylazo]-2-naphthalenesulfonic acid, disodium salt.

9. A method according to claim 4, wherein the compound is 6-amino-5-[4-(m-fluorobenzamido)-2-sulfophenylazo]-4-hydroxy-2-naphthalenesulfonic acid, disodium salt.

10. A method according to claim 4 wherein the compound is 6-amino-5-(4-benzamido-2-sulfophenylazo)-4-hydroxy-2-naphthalenesulfonic acid, disodium salt.

11. A method of inhibiting the complement system in a warm-blooded animal which comprises internally administering to said animal an effective complement inhibiting amount of a compound of the formula:

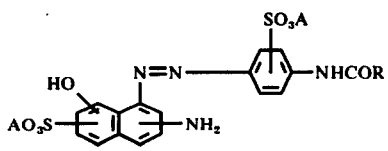

wherein R is selected from the group comprising (C$_1$–C$_6$) alkyl, phenyl, sulfophenyl sodium salt, p-nitrophenyl and m-fluorophenyl; and A is hydrogen, sodium and potassium with the proviso that A is identical in the same compound.

12. A method according to claim 11, wherein the compound is 5-(4-acetamido-2-sulfophenylazo)-5-amino-4-hydroxy-2-naphthalenesulfonic acid, disodium salt.

13. A method according to claim 11, wherein the compound is 6-amino-4-hydroxy-5-(2-sulfo-p-sulfobenzamidophenylazo)-2-naphthalenesulfonic acid, trisodium salt.

14. A method according to claim 11, wherein the compound is 6-amino-4-hydroxy-5-(4-propionamido-2-sulfophenylazo)-2-naphthalenesulfonic acid, disodium salt.

15. A method according to claim 11, wherein the compound is 6-amino-4-hydroxy-5-[4-(p-nitrobenzamido)-2-sulfophenylazo]-2-naphthalenesulfonic acid, disodium salt.

16. A method according to claim 11, wherein the compound is 6-amino-5-[4-(m-fluorobenzamido)-2-sulfophenylazo]-4-hydroxy-2-naphthalenesulfonic acid, disodium salt.

17. A method according to claim 11, wherein the compound is 6-amino-5-(4-benzamido-2-sulfophenylazo)-4-hydroxy-2-naphthalenesulfonic acid, disodium salt.

* * * * *